(12) United States Patent
Mortara (10) Patent No.: US 6,850,796 B1
(45) Date of Patent: Feb. 1, 2005

(54) METHOD AND APPARATUS TO OPTIMALLY MEASURE CARDIAC DEPOLARIZATION/REPOLARIZATION INSTABILITY

(76) Inventor: David W. Mortara, 8450 N. River Rd., River Hills, WI (US) 53217

( * ) Notice: Subject to any disclaimer, the term of this patent is extended or adjusted under 35 U.S.C. 154(b) by 240 days.

(21) Appl. No.: 09/634,271

(22) Filed: Aug. 8, 2000

Related U.S. Application Data (60) Provisional application No. 60/151,614, filed on Aug. 31, 1999.

(51) Int. Cl.[7] ............................................. A61B 5/0452
(52) U.S. Cl. ..................................................... 600/517
(58) Field of Search ................................ 600/512, 508, 600/509, 515, 517, 518

(56) References Cited

U.S. PATENT DOCUMENTS

| | | | |
|---|---|---|---|
| 4,802,491 A | | 2/1989 | Cohen et al. ................ 128/702 |
| 5,474,078 A | * | 12/1995 | Hutson ........................ 600/512 |
| 5,570,696 A | | 11/1996 | Arnold et al. ............... 128/707 |
| 5,713,367 A | | 2/1998 | Arnold et al. ............... 128/704 |
| 5,921,937 A | * | 7/1999 | Davis et al. ................. 600/508 |
| 6,169,919 B1 | * | 1/2001 | Nearing et al. ............. 600/518 |

* cited by examiner

Primary Examiner—George R. Evanisko
(74) Attorney, Agent, or Firm—Andrus, Sceales, Starke & Sawall, LLP (57) ABSTRACT

A method of identifying and measuring alternans in an electrocardiographic (ECG) signal representative of the electric activity of a heart of a patient. The ECG signals from the patient are divided into individual cardiac cycles and the amplitude of four segments of the repolarization portion and the depolarization portion of each cardiac cycle are measured. The amplitude for each of the repolarization segments are measured from a reference baseline that is determined by a first base segment occurring immediately prior to the repolarization portion of the present cardiac cycle and a second base segment occurring immediately before the depolarization portion of the next cardiac cycle in the sequence. Based upon the amplitude measurements over the repolarization and the depolarization portions of each cardiac cycle, digital signal processing is applied to the measurements to generate eigenvariables. A spectral density is calculated for each of the eigenvariables, which spectral densities can be used to determine both the presence of alternans and the respiratory frequency.

16 Claims, 8 Drawing Sheets

METHOD AND APPARATUS TO OPTIMALLY MEASURE CARDIAC DEPOLARIZATION/ REPOLARIZATION INSTABILITY

CROSS REFERENCE TO RELATED APPLICATION

This application is based on and claims priority from provisional patent application Ser. No. 60/151,614 filed on Aug. 31, 1999.

BACKGROUND OF THE INVENTION

This invention relates to a method and apparatus for assessing the electrical stability of the heart. Electrical stability is characteristic of proper functioning of the heart. Electrical instabilities, characterize, or indicate, a potential for abnormal conditions, including such serious conditions as ventricular fibrillation, which may result in sudden cardiac death.

It is known that electrocardiographic (ECG) analysis may be used to identify individuals having increased risk of myocardial electrical instability. The electrocardiograms of such individuals evidence changes in the morphology or shape of the electrocardiographic signal complex. Changes in the amplitude or temporal distribution of the T-wave portion of the electrocardiographic signal complex can be used for analysis purposes. These changes in the morphology of the electrocardiographic signal may appear in every other beat of the heart so that the electrocardiographic complex will have, for example, a T-wave of one configuration in a first beat, a T-wave of a different configuration in a second beat, a T-wave configuration resembling that of the first beat in the third beat, a T-wave configuration resembling that of the second beat in the fourth beat, and so on. The alternating signal produced by this phenomena is often termed "altemans." Because the alternation occurs on an every other beat basis, the frequency of the alternating signal is 0.5 alternations/beat or 0.5 cycles per beat (CPB).

One non-invasive technique for assessing myocardial electrical stability of a given individual involves analysis of the alternation from beat-to-beat in the morphology of the electrocardiogram (ECG) complex. Such a technique is described in U.S. Pat. Nos. 4,802,491, 5,570,696, and 5,713,367. The prior art comprehends the relationship of the fluctuations in the T-wave morphology of the ECG complex with susceptibility to ventricular fibrillation. In the prior art, the presence of alternation is detected using spectral analysis of the beat-to-beat T-wave amplitude in a single ECG lead, and measuring the excess in the unique spectral line at a frequency of 0.5 alternations/beat. The reference for T-wave amplitude measurement is the onset of QRS portion of the electrocardiographic signal. Emphasis is made on the small amplitudes of alternation to be found. Given the evidence of the small nature to the effect to be detected, it is clear that successful detection of alternation will require careful optimization of variable to be measured.

SUMMARY OF THE INVENTION

The present invention comprises a method and apparatus to optimize detection of the small altemans signal. This optimization takes into account both the anticipated physiological nature of the signal's origin, and introduces optimal measures of the signal. In addition to detecting altemans, the present invention detects the respiration frequency from the ECG. Detection of the respiration frequency is useful in its own right as a monitoring parameter, and is also used in the present invention to aid in the proper detection of altemans.

Referring to the nature of the signal, present knowledge of the nature of T-wave altemans indicates that it results from variation in the repolarization segment of the depolarization/ repolarization sequence of the myocardium. This suggests that the reference for measurement of the amplitude of repolarization-specific altemans should be near the transition from depolarization to repolarization. Otherwise, variations in the state of the myocardium due to depolarization altemans may not be separated from repolarization altemans. Such a reference is used in the present invention.

Further, it can be anticipated that the sought-after repolarization altemans has both spatial and temporal characteristics. Particularly, there will be a spatial axis which presents the strongest evidence of altemans, and this axis will not, except by accident, be coincident with any of the ECG leads recorded.

Also, the repolarization altemans may be anticipated to change in amplitude during the repolarization sequence. Thus, the strongest evidence of altemans may also come from differences in the amplitude at different times in the course of repolarization, or, more generally, from linear combinations of the signal amplitudes at different times. Such linear combinations are used in the present invention. These linear combinations can be guided in part by detection specifically of the starting time of repolarization (or end of depolarization) and the end of repolarization.

Finally, present knowledge of T-wave altemans indicates that the small variations of altemans may persist well beyond the end of apparent repolarization in the surface ECG. Thus signal amplitudes beyond the apparent end of the T wave are also considered in the present invention.

Present knowledge of the nature of T-wave altemans is limited as to how long, in terms of beats, sequences of even-odd beat alternation will normally last, or what events, such as long beat-to-beat intervals or arrhythmias may change the even-odd beat phase. This means that some variation in the phase should be considered. Particularly, if the changes of phase are at some low or moderate frequency, this degree of frequency spreading will be introduced into the spectral density, and the spectral line at 0.5 alternations/ beat will not contain all the energy of alternation. Thus, contrary to the method described in the prior art, which excludes the neighboring spectral lines, the invention described herein considers spectral lines adjacent to the line at 0.5 alternations/beat as potential evidence of altemans.

The method employed in the present invention to optimize the selection of measures for use in the determination of altemans includes the reduction of the input leads to an orthogonal 3-dimensional set, and division of the repolarization sequence into four separate time segments. The resulting 12 measures (3 leads×4segments) are further arranged into 12 independent linear combinations by rank ordering of the mean-square signal amplitude contained in each using the method of singular value decomposition. It is empirically found that these linear combinations are useful for separation (and thus, distinction) of the spectral energy due to altemans, and that due to respiration.

DETAILED DESCRIPTION OF THE PREFERRED EMBODIMENT

Data Acquisition

Data acquisition for the invention is performed on "Portrait" model electrocardiograph manufactured by Mortara Instrument, Inc. of Milwaukee, Wis. This electrocardiograph acquires the 12-lead ECG at 5000 samples/sec in each lead, detects QRS's, clusters cardiac cycles according to QRS morphology, performs signal averaging of the dominant cluster, and records on removable media the resulting averages, RR intervals, and continuous ECG rhythm data. To save space and time, the rhythm data is recorded at 1000 samples/sec for each lead. The duration of the user recording is user selectable with the option to record either 2, 5, 10, 20, 40, or 60 minutes of continuous data. Particular landmarks of the ECG, including the time of QRS onset, QRS offset, and T wave offset are determined for the average complex.

The electrocardiograph selects cycles belonging to the dominant cluster according to QRS morphology for use in subsequent steps of the method.

Lead Reduction

The 12-lead ECG consists of eight independent leads, with four additional leads derived from the basic eight. The choice is which of the 12 leads to consider independent, and which to consider derived is arbitrary. The present invention may be practiced by considering leads I, II, and V1 to V6 to be independent.

The complexity of the surface ECG is ordinarily not 8-dimensional, but instead is normally describable in two or three components. This is consistent with the origin of the surface ECG, which is one of potentials resulting from electric (vector) fields within the heart, and recorded at electrodes on the torso at distances from the heart larger than the dimension of the heart itself. The recording of eight independent leads, then, provides a spatial redundancy, which can be used to reduce the effect of noise sources. This is especially relevant when the size of the signal is to be measured is expected to be small. In the present invention, the independent leads are transformed by singular value decomposition (SVD) of the covariance matrix of the samples from the average QRS obtained from the Portrait recording into eight linear combinations of the original leads. These linear combinations are rank-ordered by the mean-square amplitude of each combination. The three combinations with the highest mean-square amplitude are selected for further analysis.

In particular, the covariance matrix elements ($C_{ij}$) are calculated from:

$$C_{ij} = \Sigma y_i(n) y_j(n)$$

The values $y_i(n)$ are amplitudes at time index n and lead i of the average cycle, where i successively corresponds to lead I, II, and V1 to V6. The summation is over values of n ranging from the QRS onset to QRS offset. The SVD of the matrix C yields eigenvectors corresponding to orthogonal linear combinations (eigenleads) of the eight input leads and eigenvalues corresponding to the mean-square amplitude in each of the eigenleads. The three eigenleads with the three largest eigenvalues are selected and form the basis for the remaining analysis. These eigenleads are derived from the continuous 1000 sample/sec rhythm data by means of the transform:

$$z_k(n) = \Sigma e_{ki} x_j(n)$$

where n is an index ranging over all the continuously sampled data, the index i corresponds to leads I, II, V1 to V6, the index k corresponds to the three eigenleads, $x_j(n)$ are the amplitudes of the original continuous rhythm leads, $e_{ki}$ is the $k^{th}$ eigenvector from the singular value decomposition, the summation is over the possible values of i, and $z_k(n)$ are the resulting eigenlead amplitudes.

Measurement Variables

Figure 1:
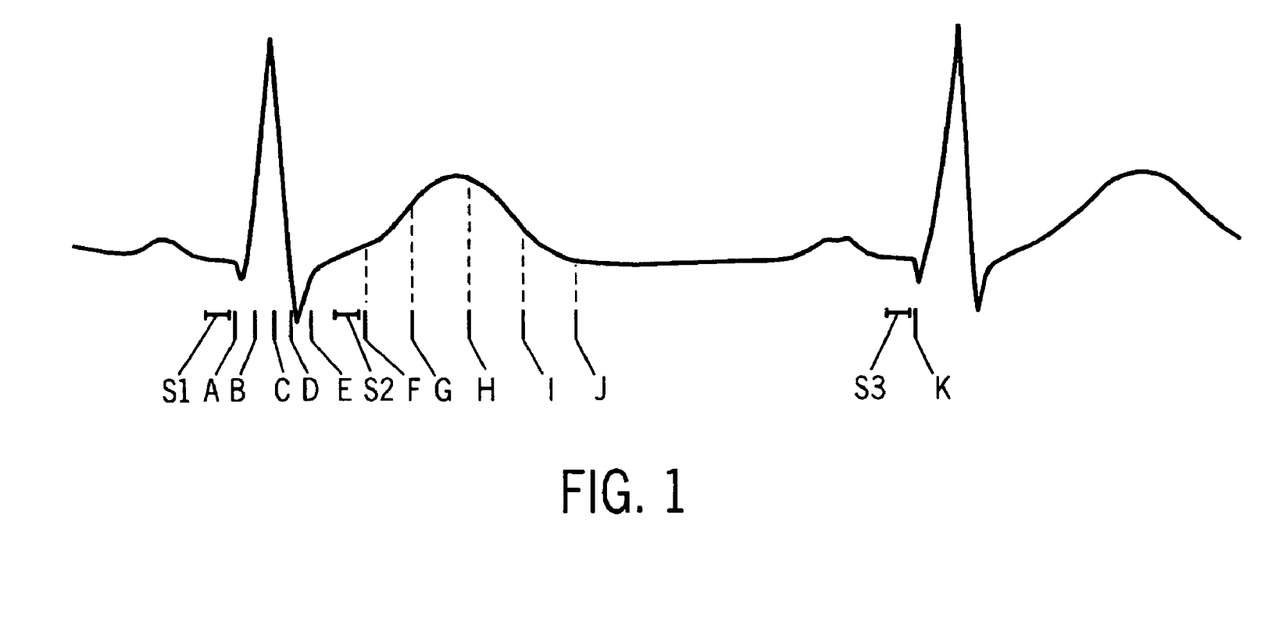
FIG. 1 shows an electrocardiograph wave form along with certain points or landmarks and segments in the wave form.

FIG. 1 represents a portion of the rhythm data from a single lead after selection of the three eigenleads. Several important data segments and landmarks are shown. The definitions of these are as follows:

Base Segment S1: A data segment starting 40 ms before QRS onset and lasting 32 ms.

Base Segment S2: A data segment starting 40 ms before landmark F and lasting 32 ms Base Segment S3: A data segment starting 40 ms before the next QRS onset and lasting 32 ms Landmark A: QRS onset Landmark B: ¼ of the QRS width after A.

Landmark C: ½ of the QRS width after A.

Landmark D: ¾ of the QRS width after A.

Landmark E: QRS offset.

Landmark F: ⅕ of the E–J interval after E

Landmark G: ⅖ of the E–J interval after E

Landmark H: ⅗ of the E–J interval after E

Landmark I: ⅘ of the E–J interval after E

Landmark J: T wave offset

Landmark K: Next QRS onset

Measurement variables for depolarization, characterized by the QRS complex, are the average amplitudes in the intervals A–B, B–C, C–D, and D–E. These amplitudes are referenced to the level of a first reference baseline drawn between base segments S1 and S3 to the middle of each base segment. The level of the reference line as it passes through the middle of base segments S1 and S3 is the average amplitude of each base segment, respectively. Measurement variables for repolarization, characterized by the T-wave, are the average amplitudes in the intervals F–G, G–H, H–I, and I–J. These amplitudes are similarly referenced to a second reference baseline drawn between segments S2 and S3.

The reference baseline for measuring repolarization amplitudes in the present invention is significantly different than that used in prior art. The prior art uses a reference level (roughly analogous to that identified as S1 in FIG. 1) established by pre-QRS amplitudes and similar to the first reference baseline the present invention uses for depolarization measures. The difference is important, because beat-to-beat variations in depolarization may leave a residual level at the end of depolarization. This residual level, because it alternates on a beat-to-beat basis, would appear as a repolarization beat-to-beat variation if the repolarization measures are referenced to the same pre-QRS levels.

Figure 2A:
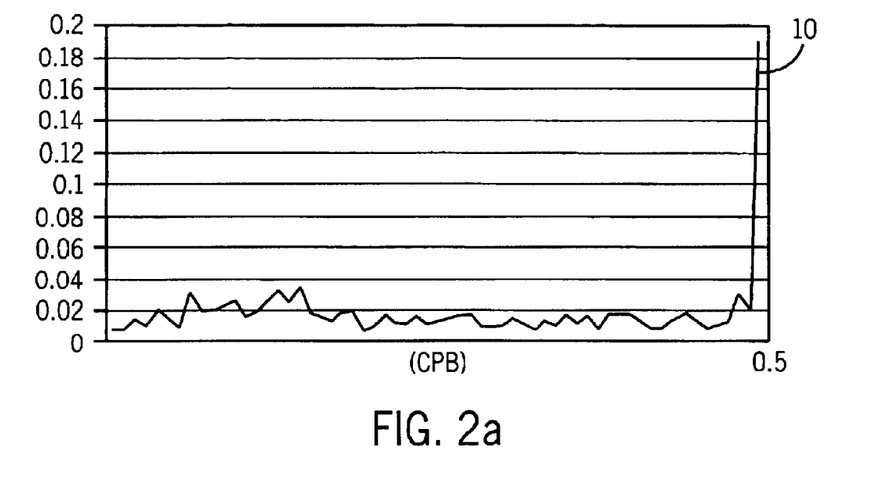
FIG. 2a shows depolarization (QRS) spectral density for a sample case.
Figure 2B:
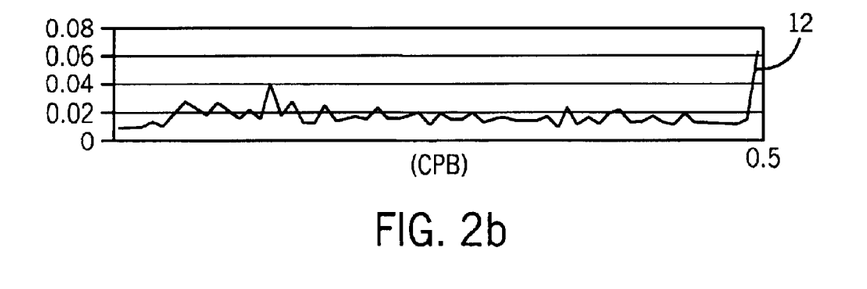
FIG. 2b shows repolarization (T-wave) spectral density for the same sample case in which the segment S2 shown in FIG. 1 is employed as the reference, as contemplated by the present invention.
Figure 2C:
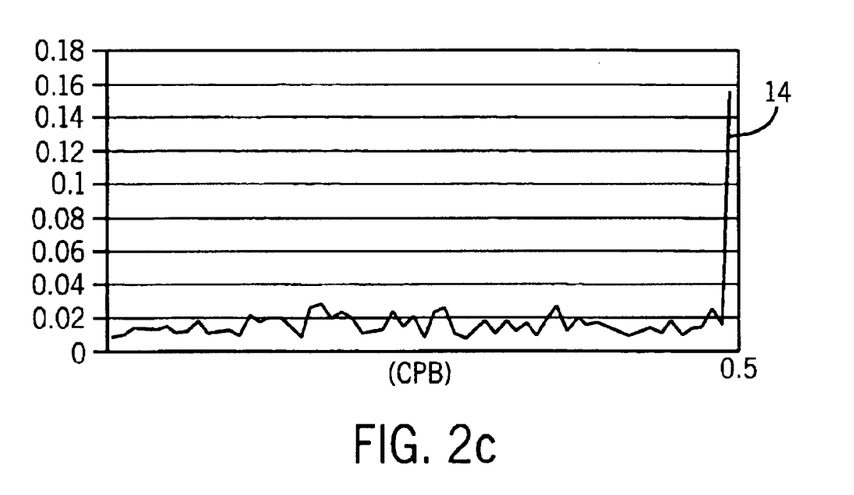
FIG. 2c shows repolarization (T-wave) spectral density for the same sample case in which the segment S1 shown in FIG. 1 is employed as the reference, as generally contemplated by the prior art.

FIGS. 2a–2c illustrate a sample case wherein the repolarization alternans amplitude is significantly overestimated when base segment S1 is used as a reference.

FIG. 2a shows that there is alternans activity 10 in the QRS spectrum. This is evidenced by the spectral peak at 0.5 cycles per beat. FIG. 2a is not, itself, an indication that there may be variations in the residual level at the end of depolarization. It is possible that the alternans phenomena is occurring in other portions of the QRS complex. However, the presence of the alternans at 0.5 cycles per beat alerts one to the fact that consideration should be given to the reference selected for the repolarization phenomena.

FIG. 2b correctly shows T-wave repolarization phenomena 12 using a post-QRS segment, i.e. base segment S2 in the reference. The use of the second reference baseline employing terminal depolarization levels eliminates the effects of variation in the residual level at the end of depolarization. That is, since both the reference and the T-wave phenomena are similarly affected by variations in residual depolarization levels, magnitudinal differences between the two are not altered by such variations.

FIG. 2c shows that with variations in the T-wave phenomena due to residual levels at the end of depolarization and use of the relatively fixed first reference baseline (pre-QRS baseline segment S1 in the example of the figure), there erroneously appears to be a significant amount of repolarization alternans 14 in the spectral density. However, this is primarily QRS, depolarization alternans rather than the T-wave, repolarization alternans phenomena employed to measure cardiac electrical instability.

Thus, it is clearly possible to incorrectly infer the presence of repolarization alternans in the presence of depolarization alternans if the incorrect reference level is used for repolarization. By referencing repolarization measures to the terminal depolarization levels (base segment S2 in FIG. 1) as shown in FIG. 2b, this error is avoided.

For both depolarization and repolarization, there are four measurements for each eigenlead. Thus, from three eigenleads, there are 12 measures in total. In addition, and as noted above, each cardiac cycle has a "usability" flag. Initially, this flag is set to usable/non-usable according to whether the acquiring device has labeled the cycle as belonging to the majority (averaged) morphology cluster, or not.

The present invention is, thus, distinct from prior art because it introduces measurement variables with the following properties:

1. Spatial, as opposed to scalar (single lead) in the prior art, measure of beat-to-beat variation, through the simultaneous inclusion of three orthogonal leads,
2. Temporal measure of beat-to-beat variation through the inclusion of four separate time segments, and
3. A repolarization-specific reference level to avoid ambiguity between depolarization and repolarization alternans.

Noise Reduction and Source Generator Isolation

The present invention anticipates measurement of signal levels comparable or smaller than may be found on individual cardiac cycles. Thus, a means of detecting and discarding noisy cycles is important. The first step in this process is the elimination of cycles whose QRS morphology does not match the average cycle. The next step is the removal by means of a high pass filter of the very low frequency part of the beat-to-beat variation of the measured variables. The high pass filter is implemented as follows.

$$v_i(n) = u_i(n) - \Sigma u_i(m)/25$$

where $u_i(n)$ is one the initial 12 unfiltered variables, $v_i(n)$ is the filtered result, n is an cardiac cycle index ranging from the first to last available and usable cardiac cycle, i is an index ranging from 1 to 12 corresponding to the particular variable, and the summation is over index m, which ranges from inclusively over the 25 usable cycles starting 12 usable cycles earlier than the index n, and ending 12 usable cycles after the index n. Whenever the index n is within 12 usable cycles of the beginning or end of the list of cardiac cycles, the summation is over the nearest 25 usable cycles It is anticipated that the beat-to-beat variation in the filtered measured variables will have multiple sources, including in most cases the effects of respiration on the ECG signal. This respiratory variation, or variation from other non-random sources, will normally have a pattern of behavior which gives rise to a correlation amongst the 12 measured variables. Detecting and isolating this correlation provides means to isolate different sources or generators of the variation. In particular, it provides means to isolate the effects of respiration and alternans. The method used to isolate the different generators of correlation is the SVD of the correlation matrix of the filtered measured variables.

$$D_{ij} = \Sigma v_i(n) v_j(n)$$

The values $v_i(n)$ are as described above, index n is an index to usable cycles, i and j are indices to the 12 measured variables. Singular value decomposition (SVD) of the 12×12 matrix D yields eigenvectors corresponding to orthogonal linear combinations (eigenvariables) of the 12 variables and eigenvalues corresponding to the mean-square amplitude in each of the eigenvariables. The eigenvariables are used for further analysis, and are obtained from:

$$w_k(n) = \Sigma f_{ki}(v_i(n) - \Sigma v_i(m)/N)$$

where n and m are indices to usable cycles, $f_{ki}$ is the $k^{th}$ eigenvector from the singular value decomposition, the first summation is over the 12 possible values of i, the second summation is over all the usable cycles, N is number of usable cycles, and $w_k(n)$ are the resulting eigenvariable values. The second term is the above expression has the purpose of ensuring that $w_k(n)$ has a zero mean. Also obtained from the SVD of the matrix D are the eigenvalues $\lambda_k$ which are recognized to be the squared standard deviation of $w_k(n)$.

The next step in the noise reduction process is the marking of cycles as unusable if the squared value of $w_k(n)$ exceeds 16 times the value of $\lambda_k$, and $\lambda_k$ exceeds 1/64 of the largest eigenvalue. This last step of noise reduction is applied only to the measures for depolarization, and only if not more than 1/8 of the initially available usable cycles have been discarded from further use by this process. Cycles marked as unusable in this part of the process are also not used during analysis of repolarization, which sequentially follows the analysis of depolarization.

Finally, this entire process of noise reduction is iterated until no further cycles are marked as unusable by the above step.

In comparison with prior art, the noise reduction steps described herein are unique. The high pass filtering of the measured variables is particularly significant because it removes a typical low-frequency, high power component of the spectral density. See, for example, FIG. 5 of U.S. Pat. No. 5,713,367. Without removal of this low-frequency component, detection and isolation of other generators of spectral energy and correlation amongst the 12 measured variables would be either less effective or obscured by the low-frequency energy. As will be seen in the following spectral estimation section, this detection and isolation contributes materially to the detection of alternans.

Autocorrelation and Spectral Estimation

Autocorrelation is a widespread technique for investigating statistical properties of a sequence. In the present invention, the autocorrelation sequence for each of the measured eigenvariables is estimated by $$R_i(m) = \Sigma w_i(n+m) w_i(n)/N$$

where N is the total number of cycles, n is an index to the cycles on the range [0,N-m], m is a lag index, and the summation is over the values of n. The values, $w_i(n)$, are the eigenvariables described above, except that wherever the index n corresponds to an unusable cycle, $w_i(n)$ takes a value of zero. The above form of the autocorrelation sequence estimator is a biased estimator, and has a smaller mean squared error than the unbiased estimator used in prior art.

Figure 3A:
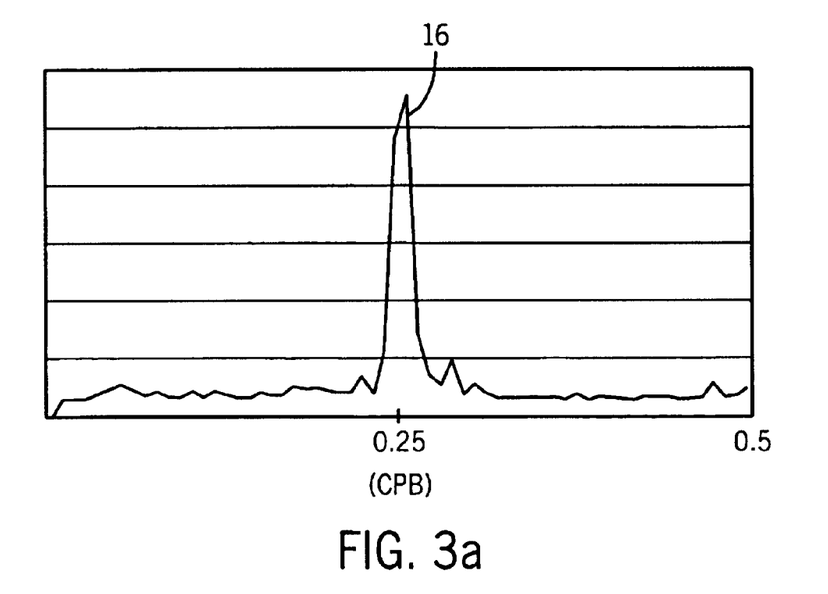
FIG. 3a shows a QRS spectrum which is a composite of the spectra of each eigenvariable.
Figure 3B:
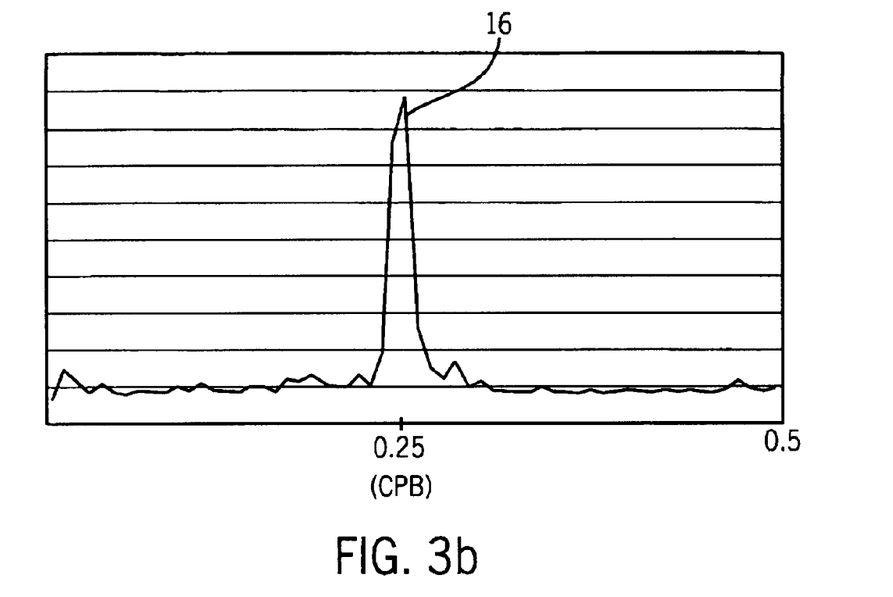
FIGS. 3b, 3c and 3d show spectra, similar to FIG. 3a, determined generally in accordance with prior art techniques showing the existence of respiration but a poor or no showing of other phenomenon such as alternans.
Figure 3C:
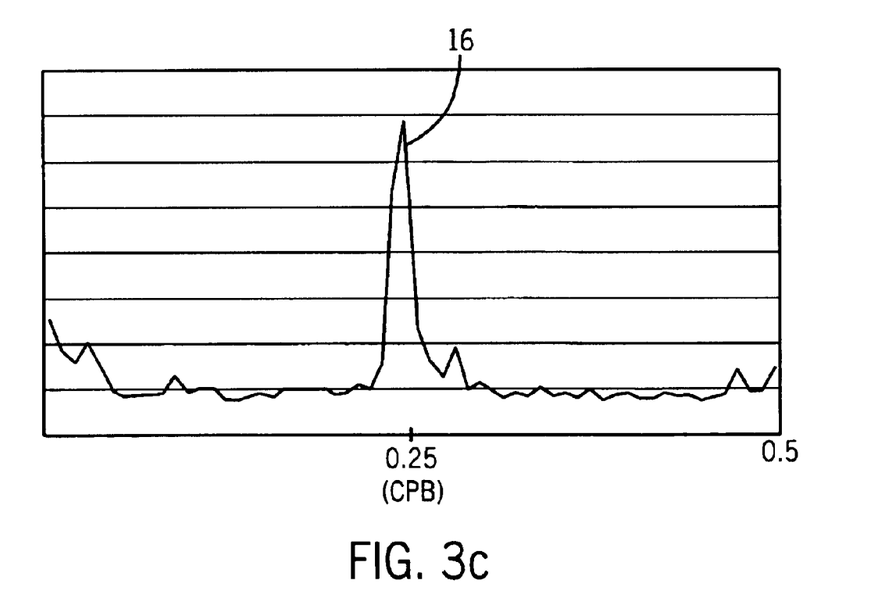
Figure 3D:
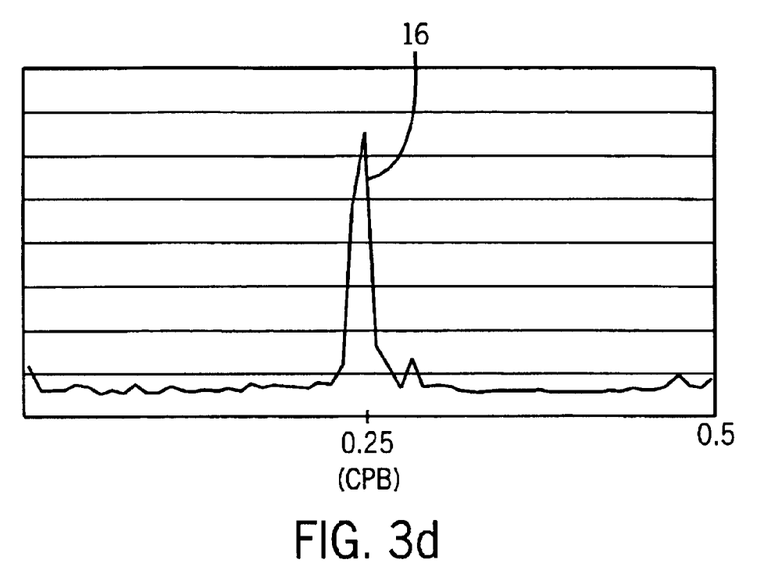

The spectral density of beat-to-beat variation is obtained from the estimated autocorrelation sequence by a discrete Fourier transform. In the present invention, an independent spectrum for each eigenvariable is available. These independent spectra can be summed to provide a single spectrum, which approximates the methods and information available in the prior art. An example of this composite spectrum is shown in FIG. 3a. FIGS. 3b, 3c, and 3d show the spectrum calculated according to the methods of the prior art (except that the first frequency bin is omitted for the prior art to keep the large 0 cycles/beat (CPB) frequency component from distorting the scale). In each of the FIGS. 3a, 3b, 3c, and 3d, the spectra are-similar, and the peak 16 at 0.25 CPB is readily visible. Without further analysis, no alternans at 0.5 CPB would be detected in this data.

Figure 3E:
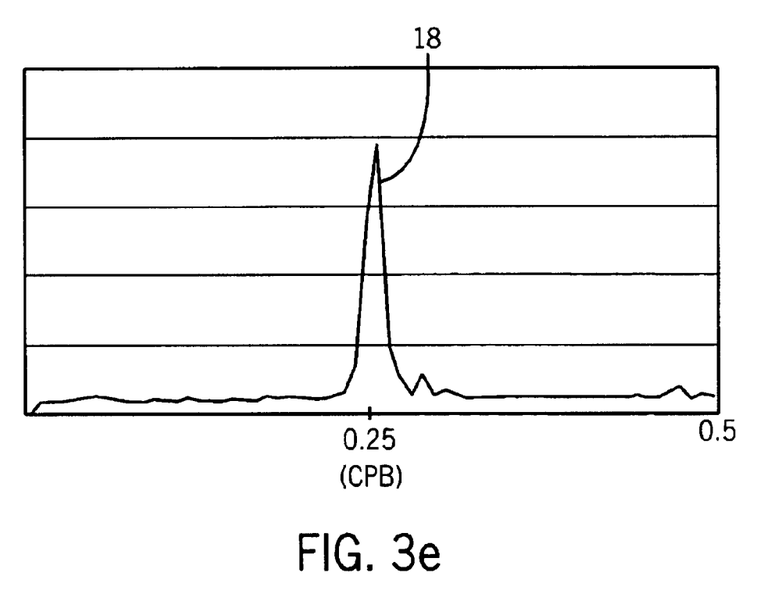
FIGS. 3e and 3f show spectra for two eigenvariables employed in the technique of the present invention.
Figure 3F:
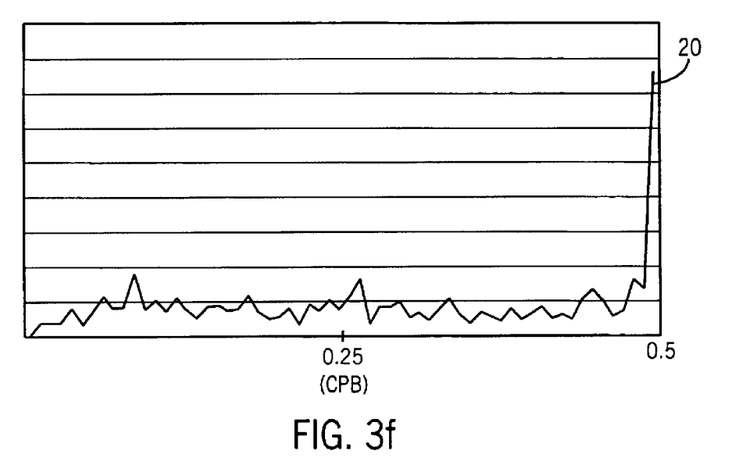

However, when the spectra for the eigenvariables are examined separately, a different result is seen. Consider FIGS. 3e and 3f, which show the spectra for two separate eigenvariables for the same patient. FIG. 3e is again similar to the prior figures, with a peak 18 at 0.25 CPB and no other distinctive features. However, FIG. 3f reveals a completely different spectrum, with a pronounced peak 20 at 0.5 CPB, and no peak at 0.25 CPB. This example illustrates the power of isolating the separate generators of the beat-to-beat variation.

The ability to identify and isolate spectral components of beat-to-beat variation which are larger and potentially detrimental to detection of alternans is a characteristic of the present invention. This ability can be exploited further in the following manner. As observed in FIG. 3, the respiratory component of the variation can readily be identified, as by the peak in FIGS. 3a–3e. This respiratory component is observed in nearly all cases. Knowledge of the frequency band of specific spectral components permits an improvement on the prior art in the estimation of the average noise spectral density and variance of spectral density. Instead of using a statistically weak small frequency segment near 0.5 CPB, the present invention uses a much larger, and therefore statistically more reliable, band from 0.03 to 0.47 CPB, excluding a band of +/−0.03 CPB about the respiratory peak. The respiratory peak is identified from the first eigenvariable spectral density of depolarization (QRS) in FIG. 3e.

Another aspect of the present invention is the ability to calculate an alternans amplitude for each cardiac cycle. This is achieved by evaluation of the linear combination of terms for a particular eigenvariable which exhibits evidence of alternans in the spectral density. Further, the alternans amplitude of a sequential series of cardiac cycles may be evaluated by assigning alternate cycles weights of −1 and 1 (or 0 in the case of omitted cycles), and subsequently summing the individual cycles amplitudes multiplied by the assigned weight. The normalized, or average, amplitude is to be obtained in this case by dividing the result by the number of non-zero weighted cycles in the sum. If the number of cycles included in the summation is a multiple of the number of cycles in a respiratory cycle, the effect of respiration on the estimated alternans amplitude will vanish. Since the amplitude of respiratory effects is often much larger than the effect of alternans, this consideration is important. Moreover, since the number of cycles/breath cycle is likely to be non-integral, the present invention uses a summation over the integral number of beats in five breath cycles to measure the alternans amplitude. The length of the respiratory cycle is determined from the peak of the respiratory spectral density measured from the QRS. The alternans amplitude may be made into a continuous, trended variable by computing the above-described amplitude for each cardiac cycle in a series, using the cycle and its N−1 precedents, where N is the integral number of cycles within five respiratory cycles.

Figure 4A:
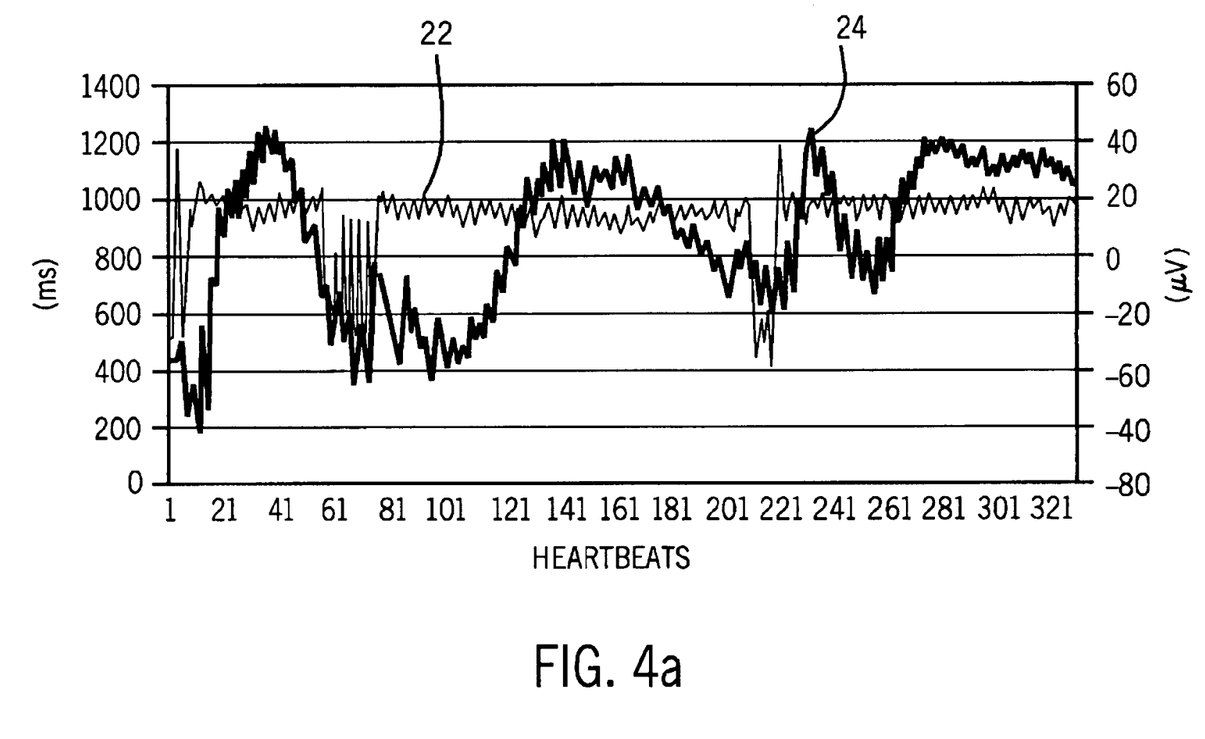
FIG. 4a shows phase characteristics of alternans amplitude.

FIG. 4a illustrates such a trend. The length of five respiratory cycles in this example is 20, which means that the measured alternans amplitude, line 22, is phase-delayed, compared to the RR interval shown by line 24, by 10 cycles. The slow alternation of the sign of the alternans is a clear indication that the even-odd beat phase (whether the even or odd cycles have positive alternans amplitude) of the alternans changes several times in the course of the ~320 beat recording. Some, but not all, of the phase may be causally linked to the RR interval irregularities. The present state of knowledge regarding phase reversal is limited.

In the prior art, there is described an attempt to account for phase reversals caused by ventricular premature beats (VPBs). One could further conjecture that short or long RR intervals without ventricular ectopy might also cause phase reversal. But it is clear from the example in FIG. 4a that reversals may happen in the absence of VPBs or other RR irregularity.

Figure 4B:
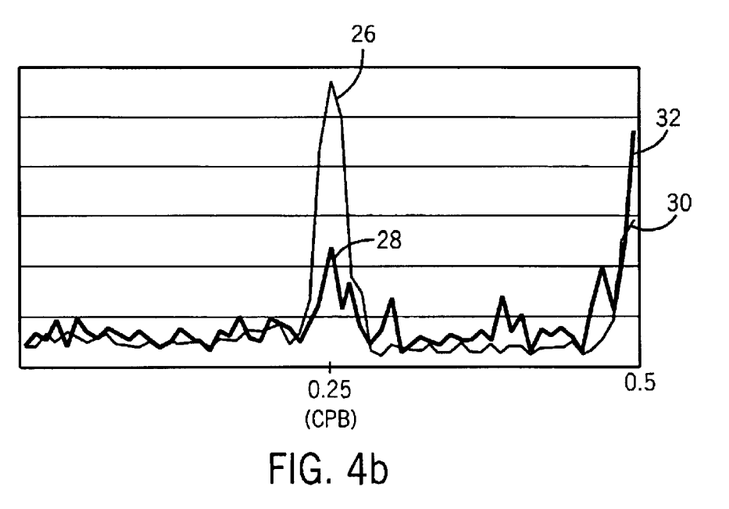
FIG. 4b shows spectra for two eigenvariables with spectral peak spreading due to phase reversals in alternans amplitude.

The phase reversals cause a spreading of the spectral peak at 0.5 CPB by an amount equal to the frequency of the reversals. This anticipated spreading is confirmed in FIG. 4b, which shows the spectra for two of the eigenvariables. Both of the spectra have peaks, 26 and 28, at the respiratory frequency of 0.25 CPB as well as 30 and 32 at 0.5 CPB. The occurrence of peaks at both frequencies raises the question of whether the peaks at 0.5 CPB might be harmonics of respiration. However, this interpretation can be ruled out for two reasons: (1) the ratio of the 0.5 CPB peak to the 0.25 CPB is not consistent between the 2 eigenvariables, and (2) the amplitude of the 0.5 CPB peak is larger than the 0.25 CPB peak for one of the eigenvariables.

In summary, the steps used to detect alternans in the present invention are as follows:

1. Acquire a five minute recording of 12-lead ECG using an electrocardiograph of the type described above
2. Perform lead reduction to three orthogonal eigenleads 3. Measure described variables in four segments in each of the three eigenleads for both depolarization and repolarization. (The repolarization segments may be located differently than as described above. In particular, locating one or more segments after the end of the QT interval may reveal alternans potentials occurring after the end of the visible T wave.)

4. For each depolarization variable, perform iteration of:

A. High pass filter the measured variables.

B. Transform measured variables to eigenvariables using singular value decomposition.

C. Exit iteration if more than 1/8 of total cycles have been removed by (D) below. If more than 1/8 of the total cycles have been removed, this is indicative that the ECG signals have excessive noise content.

D. Mark cycles (and corresponding eigenvariables) having excessive values of $w_k(n)$ and $\lambda_k$ as unusable. The remaining steps of the method are carried out using the usable cycles and corresponding eigenvariables.

5. For each repolarization variable:

A. High pass filter the measured variables.

B. Transform measured variables to eigenvariables using singular value decomposition.

6. For each eigenvariable, calculate autocorrelation sequence estimate, using a lag of up to 120 cycles.

7. For each eigenvariable, calculate spectral density from autocorrelation sequence.

8. Determine respiration frequency from maximum spectral density of the first eigenvariable of depolarization (in the range 0.03 to 0.47 CPB). This involves looking for the peak spectral density and determining the frequency at that peak.

9. For each eigenvariable, if the respiratory frequency is in the first range 0.242–0.258 CPB, or in the second range 0.158–0.174 CPB, calculate a ratio of the cumulative spectral density in the range 0.476 to 0.5 CPB to the cumulative spectral density at the respiratory peak plus to two adjacent frequency points. This ratio is designated the harmonic ratio. The harmonic ratio is zero if the respiratory frequency is not in either of the above ranges. The spectral density range 0.476–0.5 cycles per beat is the frequency range of the alternans phenomena. It is twice the first frequency range and three times the second frequency range. The harmonic ratio for the eigenvariable, either for repolarization or depolarization, with the greatest spectral density at the respiratory peak is designated as the reference harmonic ratio.

10. For each eigenvariable, calculate the average and standard deviation of spectral density on the range 0.03 to 0.47 CPB, exclusive of the respiratory frequency +/−0.03 CPB. This provides a much greater span of frequency measurement over that used in the prior art. In the prior art, a 0.40–0.46 cycles per beat frequency range has been used.

11. For each eigenvariable, and for each spectral density point, calculate an excess density, defined by the original density less the corresponding average density calculated in step 10.

12. For each eigenvariable, calculate a first alternans score equal to the excess density at 0.5 CPB divided by the corresponding standard deviation, and so further divided by the square root of 2.

13. For each eigenvariable, calculate a second alternans score equal to the excess density at 0.5 CPB plus the excess density at 0.492 CPB, divided by the corresponding standard deviation, and further divided by the square root of 3. This accommodates the fact that there can be a certain amount of spectral spreading. Thus the excess density at 0.5 cycles per beat plus the excess density at the neighboring bin of 0.492 divided by the standard deviation and by the square root of 3 is utilized.

14. For each eigenvariable, determine the alternans score as the larger of the first and second alternans scores.

15. The depolarization alternans score is the largest of all the scores for the depolarization eigenvariables for which the harmonic ratio is at least 1.5 times the reference harmonic ratio. A depolarization alternans score greater than three is considered evidence of alternans.

16. The repolarization alternans score is the largest of all the scores for the repolarization eigenvariables for which the harmonic ratio is at least 1.5 times the reference harmonic ratio. A repolarization alternans score greater than three is considered evidence of alternans.

Results from a Test Database

A database from 50 patients, all of who have an implanted automatic defibrillator, has been acquired and evaluated. The presence of the automatic defibrillator is presumptive that these patients are at risk for sudden cardiac death due to ventricular fibrillation, and thus may be expected to have a reasonable probability of exhibiting alternans. The recordings were performed while the patients were at rest. According to present knowledge of the physiological basis of alternans, recording at rest may diminish the probability of exhibiting alternans due to the lower heart rate. Ten of the 50 patients were positive for repolarization alternans, and nine were positive for depolarization alternans. When these same patients are tested according to the method of the prior art, without consideration of the harmonics of the respiration, 3 were positive for repolarization alternans, and none were positive for depolarization alternans.

It is recognized that other equivalents, alternatives, and modifications in addition to those expressly stated, are possible and within the scope of the present invention.

What is claimed is:

1. A method for identifying and measuring electrocardiographic alternans from at least one electrocardiographic (ECG) signal representative of the electric activity of a heart of a patient, the method comprising the steps of:

obtaining the ECG signal over a predetermined number of cardiac cycles of the patient's heart;

dividing the ECG signal into its individual cardiac cycles, each cardiac cycle having a depolarization portion and a repolarization portion;

dividing the repolarization portion of each cardiac cycle into a plurality of repolarization segments;

separately measuring the amplitude of each of the plurality of repolarization segments contained in the repolarization portion during each cardiac cycle, the amplitude of each repolarization segment for each cardiac cycle being measured from a repolarization reference baseline drawn between a first base segment occurring immediately prior to the repolarization portion of the present cardiac cycle and a second base segment occurring immediately prior to the depolarization portion of the subsequent cardiac cycle; and digitally processing the amplitude measurements for the repolarization segments to determine the presence of alternans in the physiologic signals.

2. The method of claim 1 wherein the step of obtaining the ECG signal includes:

obtaining a twelve lead ECG signal over the predetermined number of cardiac cycles; and reducing the twelve lead ECG signal to an orthogonal 3-dimensional lead set.

3. The method of claim 2 wherein the step of reducing the twelve lead ECG signal to the 3-dimensional set includes the steps of:

deriving eight orthogonal leads from the twelve lead ECG signal where the eight orthogonal leads are linear combinations of the twelve ECG signal leads; and selecting the three leads of the eight orthogonal lead ECG signal that have the largest mean-square amplitude.

4. The method of claim 1 further comprising the step of measuring the amplitude of a plurality of depolarization segments contained in the depolarization portion of each cardiac cycle, the amplitude of each depolarization segment being measured from a second reference baseline defined by a third base segment occurring immediately prior to the depolarization portion of the present cardiac cycle and the second base segment occurring immediately prior to the depolarization portion of the subsequent cardiac cycle.

5. The method of claim 4 wherein the ECG signal includes three ECG signals taken from three leads and the amplitude of the repolarization portion of each cardiac cycle is measured at four repolarization segments for each of the three leads, such that twelve amplitude measurements are taken over the repolarization portion of each cardiac cycle.

6. The method of claim 5 wherein the digital processing of the twelve amplitude measurements for the repolarization segments includes:

filtering the amplitude measurements to remove the low frequency portion of each measurement;

transforming the twelve amplitude measurements into eigenvariables by using singular value decomposition; and calculating a spectral density from each of the eigenvariables, wherein the spectral density for each of the eigenvariables are used to locate alternans.

7. The method of claim 5 wherein the ECG signal includes three ECG signals taken from three leads and the amplitude of the depolarization of each cardiac cycle is measured at four depolarization segments for each of the three leads, such that twelve amplitude measurements are taken over the depolarization portion of each cardiac cycle.

8. The method of claim 7 wherein the digital processing of the twelve amplitude measurements of the depolarization portion of each cardiac cycle includes:

filtering the amplitude measurements to remove the low frequency portion of each amplitude measurement;

transforming the twelve amplitude measurements of the depolarization portion into eigenvariables by using singular value decomposition;

calculating a spectral density from each of the eigenvariables; and determining the respiration frequency from the maximum spectral density of the first eigenvariable calculated from the depolarization portion of the cardiac cycle.

9. A method for identifying and measuring electrocardiographic alternans from at least one electrocardiographic (ECG) signal representative of the electric activity of a heart of a patient, the method comprising the steps of:

obtaining the ECG signal over a predetermined number of cardiac cycles of a patient's heart;

dividing the ECG signal into its individual cardiac cycles, each cardiac cycle having a depolarization portion and a repolarization portion;

dividing the repolarization portion of each cardiac cycle into a plurality of repolarization segments;

separately measuring the amplitude of the plurality of repolarization segments contained in the repolarization portion during each cardiac cycle, the amplitude of each repolarization segment being measured from a repolarization reference baseline calculated from the ECG signal for only the present cardiac cycle; and digitally processing the amplitude measurements from the plurality of repolarization segments for each cardiac cycle to determine the presence of alternans in the physiologic signals.

10. The method of claim 9 wherein the repolarization reference baseline is drawn between a first base segment occurring immediately prior to the repolarization portion of the present cardiac cycle and a second base segment occurring immediately prior to the depolarization portion of the subsequent cardiac cycle.

11. The method of claim 9 wherein the ECG signal includes three ECG signals taken from three leads and the amplitude of the repolarization portion of each cardiac cycle is measured at four repolarization segments for each of the three leads, such that twelve amplitude measurements are taken over the repolarization portion of each cardiac cycle.

12. The method of claim 11 wherein the digital processing of the twelve amplitude measurements for the repolarization segments includes:

filtering the amplitude measurements to remove the low frequency portion of each measurement;

transforming the twelve amplitude measurements into eigenvariables by using singular value decomposition; and calculating a spectral density from each of the eigenvariables, wherein the spectral density for each of the eigenvariables are used to locate alternans.

13. The method of claim 9 wherein the step of obtaining the ECG signal includes:

obtaining a twelve lead ECG signal over the predetermined number of cardiac cycles; and reducing the twelve lead ECG signal to an orthogonal 3-dimensional lead set.

14. The method of claim 13 wherein the step of reducing the twelve lead ECG signal to the 3-dimensional set includes the steps of:

deriving eight orthogonal leads from the twelve lead ECG signal where the eight orthogonal leads are linear combinations of the twelve ECG signal leads; and selecting the three leads of the eight orthogonal lead ECG signal that have the largest mean-square amplitude.

15. The method of claim 9 further comprising the step of separately measuring the amplitude of a plurality of depolarization segments contained in the depolarization portion during each cardiac cycle, the amplitude of each depolarization segment being measured from a second reference baseline.

16. The method of claim 15 wherein the second reference baseline is drawn between by a third base segment occurring immediately prior to the depolarization portion of the present cardiac cycle and a second base segment occurring immediately prior to the depolarization portion of the subsequent cardiac cycle.

* * * * *